US005655526A

United States Patent [19]
Gibertoni

[11] Patent Number: 5,655,526
[45] Date of Patent: Aug. 12, 1997

[54] DISPOSABLE ANTIBACTERIAL FILTER PARTICULARLY APPLICABLE TO LINES FOR CONNECTION TO SPIROMETRIC DEVICES

[75] Inventor: Lucio Gibertoni, Mirandola, Italy

[73] Assignee: Mallinckrodt Medical S.p.A., Mirandola, Italy

[21] Appl. No.: 239,775

[22] Filed: May 9, 1994

[30] Foreign Application Priority Data

May 14, 1993 [IT] Italy .................. MI93A0999

[51] Int. Cl.$^6$ .............. A61M 16/00; A62B 7/00
[52] U.S. Cl. .............. 128/205.27; 128/205.29; 128/205.12; 128/911; 128/912
[58] Field of Search .............. 128/205.12, 205.29, 128/207.14, 205.27, 205.28, 202.28, 202.29, 909, 203.11, 911, 912; 55/495, 505, 374, 376, 381

[56] References Cited

U.S. PATENT DOCUMENTS

| 3,228,175 | 1/1966 | Zahn et al. | 55/505 |
|---|---|---|---|
| 3,369,348 | 2/1968 | Davis | 55/374 |
| 3,659,589 | 5/1972 | Lambert | 128/726 |
| 4,015,961 | 4/1977 | Howard et al. | 55/381 |
| 4,157,902 | 6/1979 | Tokas | 55/505 |
| 4,344,781 | 8/1982 | Higgins et al. | 55/381 |
| 4,798,676 | 1/1989 | Matkovich | 128/206.16 |
| 5,020,529 | 6/1991 | Gobin | 128/909 |

FOREIGN PATENT DOCUMENTS

| 880797 | 4/1943 | France . |
| 3039916 | 5/1981 | Germany . |

Primary Examiner—Edgar S. Burr
Assistant Examiner—V. Srivastava
Attorney, Agent, or Firm—Guido Modiano; Albert Josif

[57] ABSTRACT

Disposable antibacterial filter particularly applicable to lines for connection to spirometric devices, including a filter body which is substantially bag-shaped and is connected, at its open end, to a sleeve that can be coupled to the connecting hose of a spirometric device and acts as mouthpiece for the user.

2 Claims, 1 Drawing Sheet

U.S. Patent  Aug. 12, 1997  5,655,526
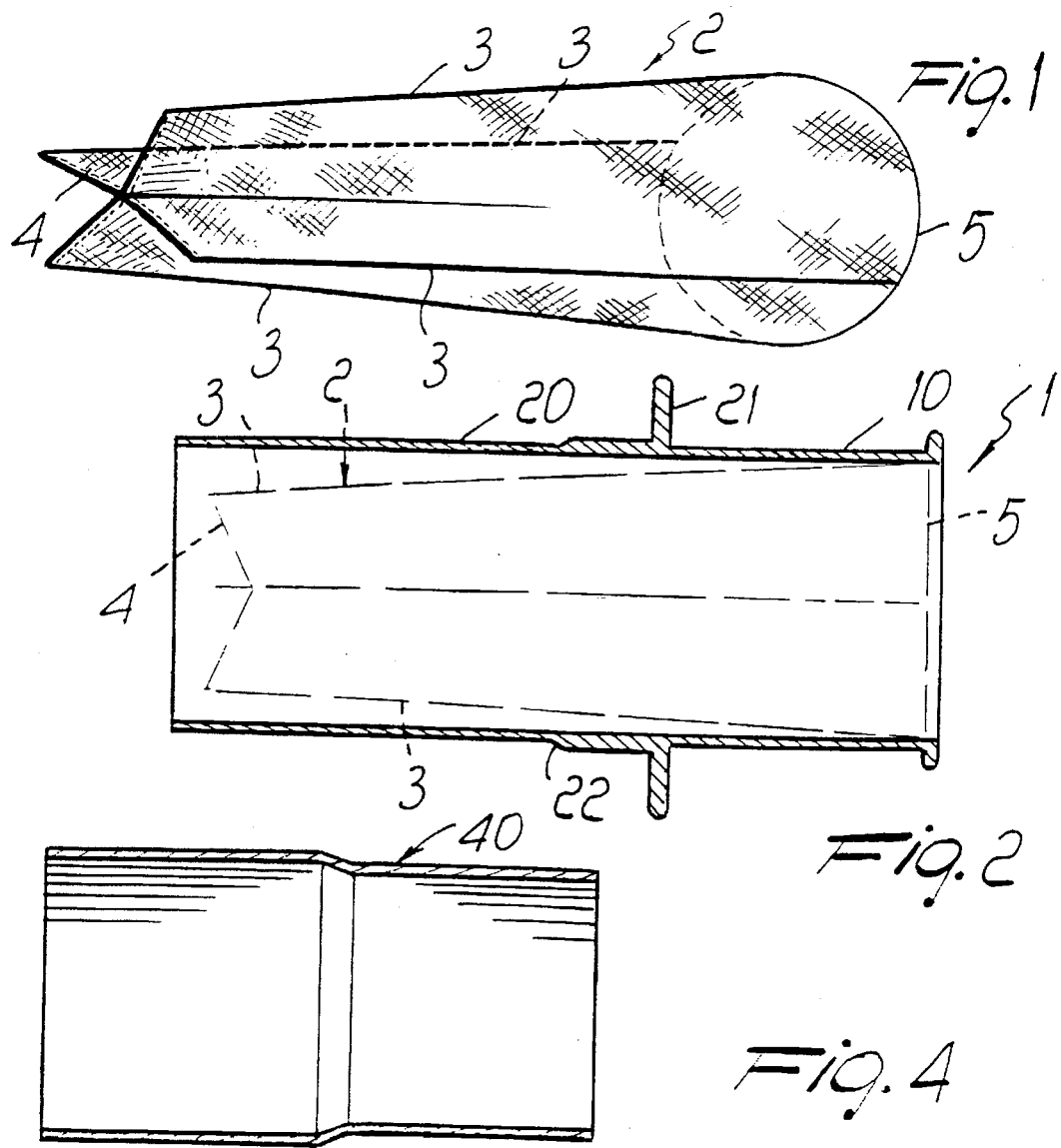
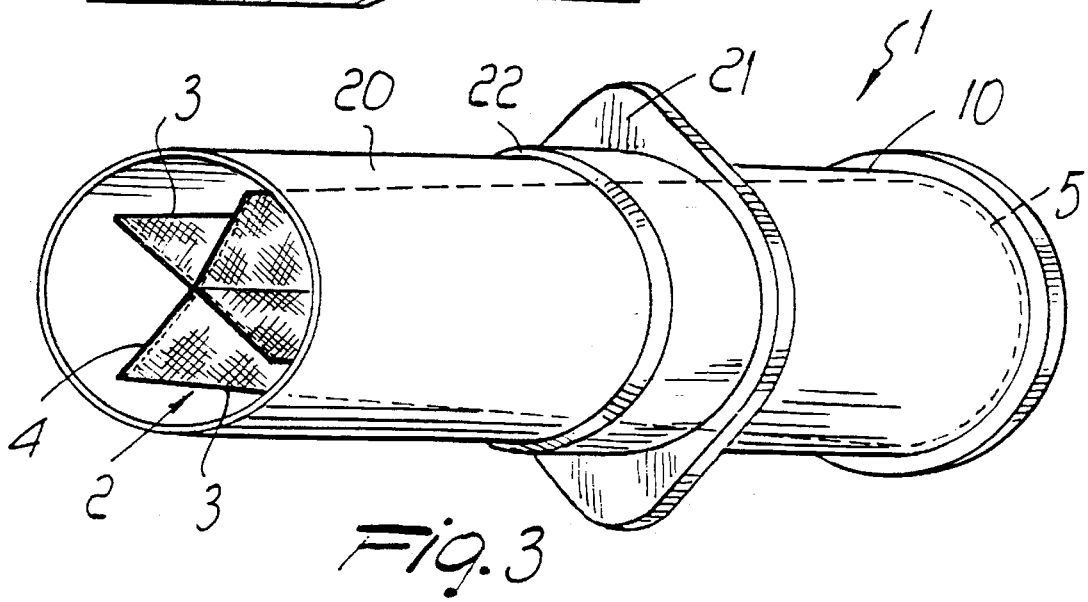

DISPOSABLE ANTIBACTERIAL FILTER PARTICULARLY APPLICABLE TO LINES FOR CONNECTION TO SPIROMETRIC DEVICES

BACKGROUND OF THE INVENTION

The present invention relates to a disposable antibacterial filter device particularly applicable to lines for connection to spirometric devices.

As it is known, spirometric devices are frequently used in respiratory physiopathology and bronchopneumology wards and in sports medicine centers.

The spirometric technique is used to determine the volume of the inspired air or to study the composition of the expired air in order to ascertain the functionality of the lungs and of the basal metabolism.

The patient undergoing a spirometric test must breathe into the spirometer through a plastic hose which is provided with a mouth-nose mask or with a mouthpiece that allows to convey the air to the device.

Since most of the patients undergoing this test may be affected by respiratory disorders, there is the problem that the viral and bacterial loads present in the air expired by a patient during the spirometric test are carried through the hose to the device, which is thereby contaminated.

The bacterial contamination of the spirometer and of the hose may therefore be transmitted to the patients that are subsequently subjected to the same test.

In order to prevent any possibility of contamination of the device and of the hose as well as any cross-contamination, antibacterial filters interposed between the hose and the mask or mouthpiece have already been used.

The filter must have an extremely low flow resistance to avoid altering the respiratory parameters recorded during the spirometric test and must also have a good bacterial retention ability.

The filters currently in use comprise a box-like container inside which there is an antibacterial filtration membrane which is pleated and arranged in a pack-like configuration.

First of all, with this arrangement the filtration surface is considerably limited, so that antibacterial effectiveness may be severely compromised.

Another drawback resides in the fact that these kinds of filters have a very high cost and their disposable use is consequently particularly expensive.

Furthermore it is necessary to replace, beyond the filter body, the mouthpiece or mask which is in contact with the user.

SUMMARY OF THE INVENTION

The principal aim of the present invention is to solve the problems described above by providing an antibacterial filter that is designed specifically for spirometric devices and allows to offer a very large actual filtration surface, together with the possibility of providing an extremely low flow resistance.

Another aim of the invention is to provide a disposable antibacterial filter device which is structurally very simple, allowing to significantly reduce its production costs.

Another aim of the present invention is to provide a disposable antibacterial filter device which, due to its particular constructive characteristics, is capable of giving the greatest assurances of reliability and safety in use.

An object of the present invention is to provide a disposable antibacterial filter device which can be easily obtained starting from commonly commercially available elements and materials and is furthermore competitive from a merely economical point of view.

According to the invention, there is provided a disposable antibacterial filter device that can be applied particularly to lines for connection to spirometric devices, which comprises a filter body which is substantially bag-shaped and is connected, at its open first end, to a first end of a sleeve, which sleeve can be coupled to the connecting hose of a spirometric device and acts as mouthpiece for the user. The device can also comprise a skirt defining a cylindrical perimetric surface, the skirt being connected to a second end of said sleeve. The filter body has a substantially circular open first end and a closed second end and comprises longitudinal folds. The folds are closed at the closed second end of the filter body along cross-like joining lines, the cross-like joining lines forming a substantially central joining point. The filter body is arranged inside the sleeve.

BRIEF DESCRIPTION OF THE DRAWINGS

Further characteristics and advantages of the invention will become apparent from the following detailed description of a preferred but not exclusive embodiment thereof, illustrated only by way of non-limitative example in the accompanying drawings, wherein:

FIG. 1 is a schematic perspective view of the bag-shaped filter;

FIG. 2 is a sectional view of the sleeve with a cylindrical skirt;

FIG. 3 is a schematic perspective view of the bacterial filter device according to the invention;

FIG. 4 is a sectional view of an adapter coupling.

DESCRIPTION OF THE PREFERRED EMBODIMENTS

With reference to the above figures, the disposable antibacterial filter device particularly applicable to lines for connection to spirometric devices, according to the invention, is generally designated by the reference numeral 1 and comprises a bag-shaped body 2 which advantageously comprises a filtration membrane of a per se known type which has longitudinal folds, designated by the reference numeral 3, which are joined at their closure end by hot welding or gluing or with other similar methods so as to form a cross-like joining region 4 which closes one end of the bag, whereas the other end, designated by the reference numeral 5, can assume the usual circular open configuration.

At the open end 5, the filter body 2 can be applied to a sleeve 10 by gluing, hot welding, and so forth.

The sleeve 10 has the particularity that it forms the element for coupling to the hose for connection to the spirometric device and furthermore constitutes the mouthpiece to be used directly by the user. The sleeve 10 has, at its end for connection to the filter body, an externally protruding edge.

Said sleeve 10 can be axially shorter than the filter body or, as shown in the accompanying drawings, it can be connected to a cylindrical skirt, designated by the reference numeral 20, which advantageously is monolithic with the sleeve 10 and affects the entire axial extension of the bag-shaped body.

With this embodiment, the cylindrical skirt 20 acts as protection element for the filter device body, avoiding the possibility of breakage during handling and preventing the filter bag from being pinched inside a connection, with the risk of breakage and in any case of imperfect use, when it is coupled to the connection hose.

It should also be specified that since the filter bag is joined, at its closed end, along cross-like joining lines, during its use said filter body gradually departs from the perimetric surface of said skirt, from the open first end of the filter body to the second end of the filter body, thereby it does not adhere to the walls surrounding it, which may be constituted by the sleeve or by the hose for connection to the machine, thus allowing full use of its entire surface.

To the above it should also be added that lugs 21 may be provided between the sleeve and the skirt for forming a grip element.

Furthermore, in order to allow adaptation to the different connectors for coupling to the hoses for connection to the spirometric device, the skirt 20 has on its outer surface an expansion 22 consisting in a step region that allows to apply the filter to hoses with multiple different diameters, and it is furthermore possible to apply the adapter connector 40 which allows to cover a wider size range.

To the above it should also be added that the sleeve 10 can itself form the mouthpiece where the user's mouth is applied, or it is optionally possible to apply special mouthpieces, especially for non-cooperative patients.

From what has been described above, it is thus evident that the invention achieves the intended aim and objects, and particularly the fact is stressed that a disposable antibacterial filter with a wide filtration surface and with an extremely simple structure is provided; furthermore, in the solution provided with a cylindrical skirt, said skirt protects the filter against any contact with foreign objects and against possible crushing prior to its insertion inside the hose for connection to the spirometric device.

The invention thus conceived is susceptible to numerous modifications and variations, all of which are within the scope of the inventive concept.

All the details may furthermore be replaced with other technically equivalent elements.

In practice, the materials employed, so long as they are compatible with the specific use, as well as the contingent shapes and dimensions, may be any according to the requirements.

What is claimed is:

1. Disposable antibacterial filter device for connection to spirometric devices comprising a sleeve, a filter body connected to a first end of said sleeve, and a skirt defining a cylindrical surface, said skirt being connected to a second end of said sleeve, said filter body having a substantially circular open first end and a closed second end and comprising longitudinal folds, said folds being closed at said second closed end along cross-like joining lines, said cross-like joining lines forming a substantially central joining point, said folds forming a filtering surface which gradually departs from the surface of said skirt from said first end of said filter body towards said second end of said filter body, said filter body being connected at said open end to said first end of said sleeve and being arranged inside said sleeve, said cylindrical skirt and said filter body having substantially equal axial extensions, said device further comprising means for connecting said filter device to hoses of different diameters, said means consisting of a step region provided on the outer surface of said skirt.

2. Disposable antibacterial filter device according to claim 1, wherein said sleeve has an externally protruding edge at said end for connection to said filter body.

* * * * *